United States Patent [19]

Kessler

[11] 4,153,739

[45] May 8, 1979

[54] METHOD FOR COLLECTING BLOOD

[75] Inventor: Stephen B. Kessler, Guttenberg, N.J.

[73] Assignee: Becton, Dickinson and Company, Rutherford, N.J.

[21] Appl. No.: 811,947

[22] Filed: Jun. 30, 1977

[51] Int. Cl.² .................... A61K 47/00; B32B 17/10; B32B 27/36
[52] U.S. Cl. ...................................... 427/2; 428/417; 428/441
[58] Field of Search ...................... 428/417, 441; 427/2

[56] References Cited
U.S. PATENT DOCUMENTS

| | | | |
|---|---|---|---|
| 3,457,098 | 7/1969 | Leininger et al. | 427/2 |
| 3,914,469 | 10/1975 | Delano et al. | 428/441 |
| 4,053,666 | 10/1977 | Taylor et al. | 428/441 |

OTHER PUBLICATIONS

Chemical Abstracts, vol. 83, No. 22, 181267z, 1975.
Condensed Chemical Dictionary, A & E Rose, 1966, Reinhold, pp. 769, 770.

*Primary Examiner*—Douglas J. Drummond
*Attorney, Agent, or Firm*—Kane, Dalsimer, Kane, Sullivan and Kurucz

[57] ABSTRACT

The disclosure is of a method of maintaining the blood clot-activating properties of a siliceous surface in a blood collecting assembly. The method comprises coating the siliceous surface with a water soluble, inert, film forming barrier material. The advantage of the method of the invention is a retention of speedy clotting time. The disclosure is also of improved blood collecting assemblies wherein the clot-activating components are coated with a film barrier of a water soluble, inert, polymeric material.

7 Claims, 7 Drawing Figures

METHOD FOR COLLECTING BLOOD

BACKGROUND OF THE INVENTION

1. Field of the Invention

The invention relates to methods for the collection, clotting and separation of the light, liquid portion of blood from the heavy, substantially cellular portion of blood and more particularly relates to a method of maintaining the blood clot activating property of a clot activator employed in such method.

2. Brief Description of the Prior Art

The length of time required for blood collected in a blood collection assembly to clot after its removal from the mammalian body is dependent upon a number of interrelated, little understood factors. The time taken to form a blood clot in collected blood is dependent to some extent on the rate of conversion of prothrombin to thrombin and of fibrinogen to fibrin. One of the factors which increases the rate of clot formation is exposure of the blood to "siliceous" materials such as glass, silica, kaolin, bentonite, siliceous aluminum hydrate and diatomaceous earth or kieselguhr; see for example Soulier et al, British Journal of Haemetology, Vol. 6, pages 88 through 101 (1960).

Recently, blood collection assemblies for the separation of blood into its light liquid and heavy, substantially cellular phases have been proposed which include gel-like silicone compositions having a density intermediate between the light, liquid phase and the heavy, substantially cellular phase of blood. These gel materials are placed in the container component of a blood collection system and sealed therein for subsequent use as a barrier between the blood phases; see for example U.S. Pat. Nos. 3,852,194; 3,852,194; 3,920,549; and 3,997,442. In addition, it has also been proposed to add particles of siliceous materials to the container component of the blood collection system; see for example French Pat. No. 2,290,665.

In general, the prior art methods and apparatus are not totally satisfactory for the collection of blood and its subsequent separation into light, liquid phases and heavy, substantially cellular phases. The difficulty arises in that over a period of time the silicone based barrier gels give rise to vapors and spreading liquid films. The vapors eventually condense on the glass walls of the container and/or on the surfaces of the clot activator particles. The condensed vapors and the liquid films form a barrier on the activator surfaces as well as on the glass container walls. Subsequently, when blood is introduced into the container, it is prevented from contacting the activator particle surfaces and/or the glass container walls. Thus, one of the factors which promotes the enzymatic conversion of clot forming materials to blood clots is prevented from functioning.

By the method of my invention, the blood clot activating properties of the glass and/or activator particles is maintained during storage even over relatively long periods. When the blood is introduced into the blood container, the container glass wall and/or activator particles become available for contact with the blood to promote clot formation.

SUMMARY OF THE INVENTION

The invention comprises a method of maintaining the blood clot activating property of a siliceous surface in a blood collecting assembly which includes a substance with the potential of contacting the surface and deactivating said property, which comprises; coating the siliceous surface with a water soluble, inert, film forming barrier material.

DETAILED DESCRIPTION OF THE PREFERRED EMBODIMENTS OF THE INVENTION

A complete understanding of the invention may be conveniently obtained by the reading of the following description in conjunction with the drawings of FIGS. 1 through 7, inclusive.

Figure 1:
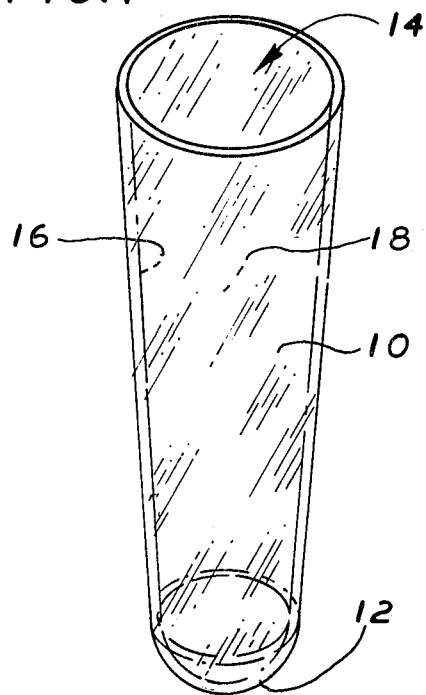
FIG. 1 is an isometric view of a tubular blood collection container.

FIG. 1 shows an embodiment tubular blood collection container 10 having a closed first end 12 and an open second end 14 leading to bore 18. The bore 18 is defined by the ends 12, 14 and the inside wall 16 of the container 10. The container 10 forms a collection container component for a blood collection apparatus as will be described more fully hereinafter. In general it can be said that blood is introduced into the bore 18 of container 10 wherein it is brought into contact with the inner walls 16 of the container. Container 10 is fabricated from glass so that the inner wall 16 functions as a blood clot activating agent when blood is brought into the bore 18.

Figure 2:
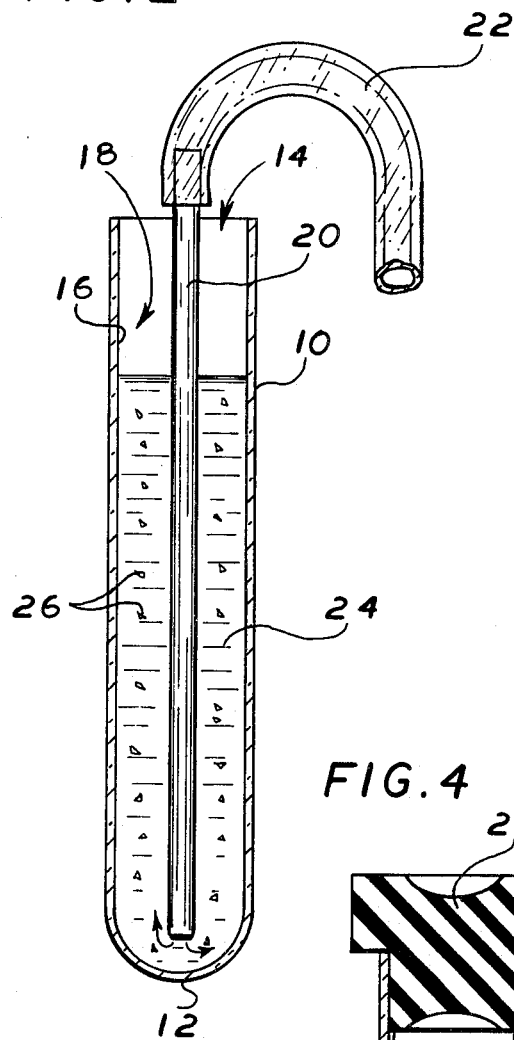
FIG. 2 is a cross sectional side elevation of the embodiment tube shown in FIG. 1, being treated according to the method of the invention.

According to the method of the invention, the blood clot activating property of the inner wall 16 is maintained by coating the wall 16 with a water soluble, inert, film forming barrier material. Referring now to FIG. 2, a cross sectional side elevation of tube 10, one can see the first step in a preferred method of the invention. As shown in FIG. 2, a cannula 20 has been introduced into bore 18 of the container 10 and a protective, water soluble, inert film forming barrier material 24 dispensed into the bore 18 from cannula 20 which is supplied from a storage vessel (not shown in FIG. 2) by tube 22. The film forming barrier material 24 has dispersed therein particles of a siliceous material such as silica particles 26. Advantageously, the particles 26 are particles of a high purity crystalline silica such as Min-U-S:1 5 (Pennsylvania Glass Sand Corp.). The maximum size of particles 26 are preferably between about 0.4 and 20 microns in diameter.

The film forming barrier material 24 must be water soluble and inert with respect to blood and blood testing reagents. The term "inert" as used herein means that the film forming barrier material 24 and barriers formed therefrom will not enter into or otherwise adversely affect the desired separation of the light, liquid phase of blood from the heavy, substantially cellular phase nor will it interfere with conventional diagnostic tests to be performed upon either component phase of the blood. Representative of film forming barrier material 24 are coating preparations of polyvinylpyrrolidone, poly(ethylene oxide) and like water soluble polymers. The following is an example of a typical composition which may be employed as the film forming barrier material 24.

Preparation 1

To isopropanol, add 1% by weight polyvinylpyrrolidone and 1% by weight of silica having an average diameter of 1.5 microns. The resulting mixture is mixed thoroughly in a blender or homogenizer.

Figure 3:
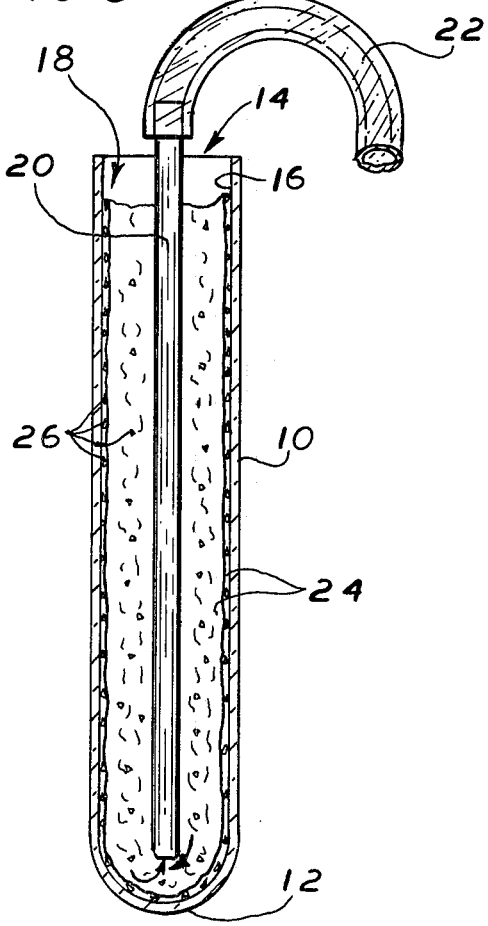
FIG. 3 is a view as shown in FIG. 2 but following treatment.
Figure 4:
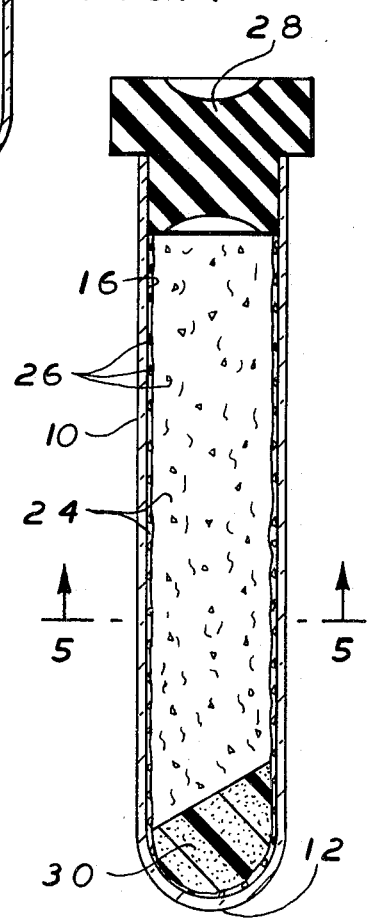
FIG. 4 is a cross sectional side elevation of a treated blood collection container ready for use.
Figure 5:
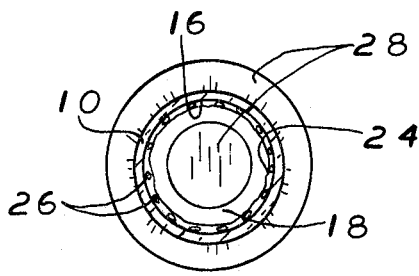
FIG. 5 is a cross sectional view along lines 5—5 of FIG. 4.

Referring now to FIG. 3, a cross sectional side elevation as seen in FIG. 2, one may see that the bulk of the film forming barrier material 24 has been evacuated from bore 18 through the cannula 24 and tube 22 to return to the storage vessel. Left on the inner walls 16 of the tubular container 10 is a thin coating of the film forming barrier material 24 including particles of silica 26. The solvent employed in preparing the film forming barrier material (isopropanol in the Preparation 1) is allowed to evaporate leaving a film of the water soluble polyvinyl pyrrolidone covering the inner wall 16 of tubular container 10. When the barrier material is fully formed as a film on the inner wall 16 of tube 10, a silicone based gel material such as that described in U.S. Pat. No. 3,920,549 may then be positioned in the bottom of the tube 10 as shown in FIG. 4, a cross sectional side elevation of the completed blood collection container component of a blood collection assembly. A stopper 28 is inserted in the open end 14 of container 10 with the gel barrier material 30 in the lower end of bore 18. Generally, such blood collection containers are at least partially air evacuated so that they may draw blood into the bore 18 when a needle bearing cannula is inserted through the cannula penetrable stopper 28. Referring now to FIG. 5, a cross sectional view along lines 5—5 of FIG. 4 one may see the details of the film formed on the inner wall 16 of container 10. The closed tube 10 shown in FIGS. 4 and 5 may be stored for extended periods of time before use. If storage conditions are such that vapors or liquid films are generated from the gel material 30, such contaminations may contact only the film protected inner walls 16 or the lower surface of stopper 28. The embodiment blood collection container 10 is used in a conventional manner as depicted in FIGS. 6 and 7.

Figure 6:
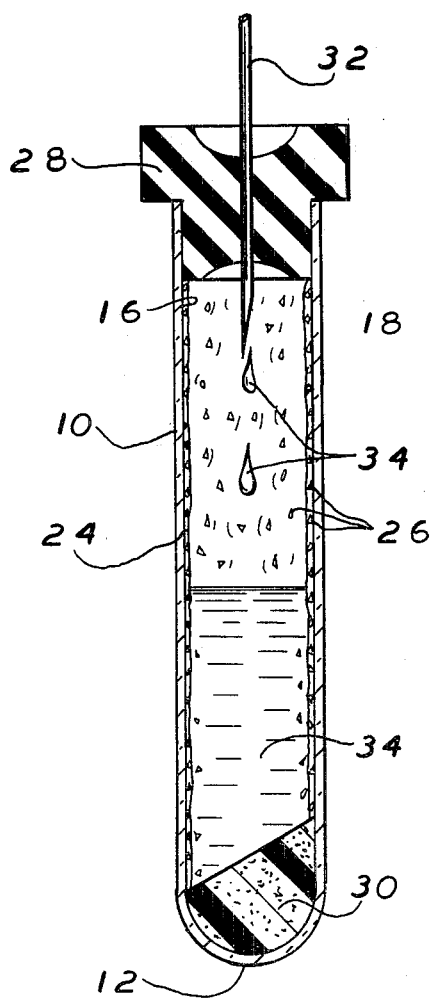
FIG. 6 is an isometric view of the embodiment container seen in FIG. 4, being filled with blood.
Figure 7:
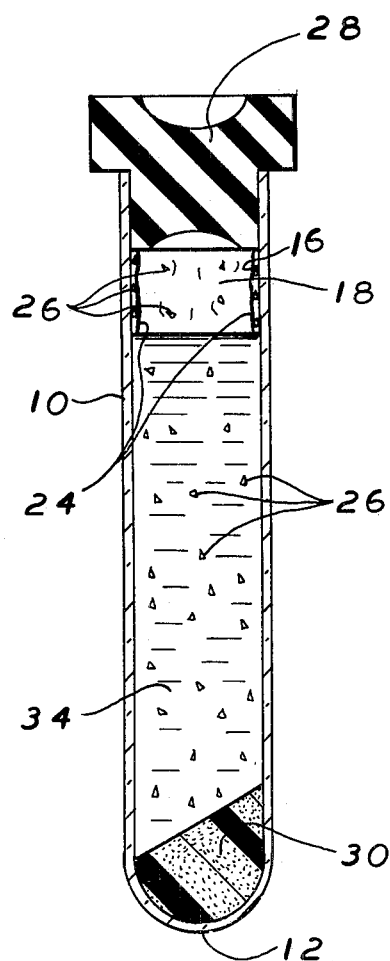
FIG. 7 is a cross sectional side elevation of the embodiment container seen in FIG. 6 but after it has been filled with blood.

FIG. 6 is a cross-section view of the tubular container 10 shown in FIGS. 4 and 5, with a blood bearing needle 32 inserted through the cannula penetrable stopper 28. Blood 34 from needle 32 is partially filling the bore 18 of container 10. As shown in the FIG. 6, the coating 24 is beginning to dissolve and release silica particles 26 to mix with the blood 34 as it enters the container 10. As shown in FIG. 7, a cross sectional side elevation of the embodiment tube 10, one may see that with completion of filling the tube 10 bore 18 with blood 34, the water soluble, barrier coating 24 has dissolved releasing the silica particles 26 to be suspended within the blood mixture. The walls 16 are also uncovered to contact blood 34. Within about 15 minutes, the blood 34 will clot. This compares favorably with control collection containers which do not bear the coating 24. In the latter instances, up to one or more hours may be required for a clot to form in blood 34.

A further advantage to the method of the invention resides in the release of the siliceous particles 26 generally throughout the volume of collected blood 34. This often obviates the necessity for agitating the blood filled container 10 to insure distribution of the particles 26 so that a uniform clotting action is obtained. Those skilled in the art will appreciate however that the tube 10 shown in FIG. 7 may also be agitated to further assure dispersing of the particles 26 throughout the volume of the collected blood 34.

Following the filling of the tubular blood collection container with blood, separation of the blood is carried out in a conventional manner, i.e.; by centrifuging the blood filled container until the blood separates into its light liquid and heavy, cellular phases with the gel material 30 forming a physical and chemical barrier between the separate phases. Techniques for affecting the actual physical and chemical separation of the blood phases are well known; see for example U.S. Pat. Nos. 3,920,549 and 3,997,442.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

We claim:

1. A method of manufacturing a storage stable blood collection assembly including a siliceous surface component for blood clot activation and a silicone based gel with a potential of contacting the surface and deactivating blood clot activation, which comprises;
    providing the siliceous surface component;
    coating the siliceous surface with a water soluble, inert, film forming barrier material; and
    disposing said silicone based gel within the assembly whereby it may come into contact with the coated surface.

2. The method of claim 1 wherein said siliceous surface is silica.

3. The method of claim 1 wherein said siliceous surface is the glass blood collecting container.

4. The method of claim 1 wherein said film forming barrier material is a solution of poly(ethylene oxide).

5. The method of claim 1 which further comprises forming a film of said barrier material on the siliceous surface.

6. A method of maintaining the blood clot activating property of a siliceous surface in a blood collecting assembly which includes a substance with a potential of contacting the surface and deactivating said property, which comprises;
    coating the siliceous surface with a water soluble, inert, film forming solution of polyvinylpyrrolidone.

7. A method of maintaining the blood clot activating property of a siliceous surface in a blood collecting assembly which includes a substance with a potential of contacting the surface and deactivating said property, wherein said siliceous surface comprises particles selected from the class consisting of glass, kaolin, bentonite, siliceous aluminum hydrate, diatomaceous earth and kieselguhr, which comprises;
    suspending said particles in a water soluble, inert, film forming barrier material; and
    disposing the suspension in the blood collection assembly wherein it will come into contact with collected blood.

* * * * *